(12) United States Patent
Shaw et al.

(10) Patent No.: US 11,298,467 B2
(45) Date of Patent: Apr. 12, 2022

(54) SYRINGE WITH MULTIFUNCTIONAL NEEDLE HOLDER AND RETAINER RING ASSEMBLY

(71) Applicants: Retractable Technologies, Inc., Little Elm, TX (US); Thomas J. Shaw, Frisco, TX (US)

(72) Inventors: Thomas J. Shaw, Frisco, TX (US); Ni Zhu, Plano, TX (US); Jordan Duesman, Pilot Point, TX (US)

(73) Assignee: Retractable Technologies, Inc., Little Elm, TX (US)

( * ) Notice: Subject to any disclaimer, the term of this patent is extended or adjusted under 35 U.S.C. 154(b) by 529 days.

(21) Appl. No.: 16/286,958

(22) Filed: Feb. 27, 2019

(65) Prior Publication Data
US 2020/0268985 A1 Aug. 27, 2020

(51) Int. Cl.
*A61M 5/32* (2006.01)

(52) U.S. Cl.
CPC ........ *A61M 5/3234* (2013.01); *A61M 5/3221* (2013.01); *A61M 2005/3239* (2013.01); *A61M 2207/00* (2013.01)

(58) Field of Classification Search
CPC .. A61M 5/3234; A61M 5/3221; A61M 5/178; A61M 5/344; A61M 2005/3239; A61M 2005/341; A61M 2207/00
See application file for complete search history.

(56) References Cited

U.S. PATENT DOCUMENTS

| | | | |
|---|---|---|---|
| 4,838,869 A | 6/1989 | Allard | |
| 4,973,316 A | 11/1990 | Dysarz | |
| 4,994,034 A | 2/1991 | Botich et al. | |
| 5,053,010 A | 10/1991 | McGary et al. | |
| 5,084,018 A | 1/1992 | Tsao | |
| 5,114,410 A | 5/1992 | Caralt Battle | |
| 5,201,710 A | 4/1993 | Caselli | |
| 5,211,629 A * | 5/1993 | Pressly | A61M 5/3234 604/110 |
| 5,578,011 A | 11/1996 | Shaw | |
| 5,632,733 A | 5/1997 | Shaw | |
| 6,090,077 A | 7/2000 | Shaw | |
| 6,572,584 B1 | 6/2003 | Shaw et al. | |
| 7,351,224 B1 | 4/2008 | Shaw | |
| 7,947,020 B2 | 5/2011 | Thayer | |
| 9,642,970 B2 | 5/2017 | Shaw et al. | |
| 2004/0143215 A1 | 7/2004 | Yang | |

(Continued)

*Primary Examiner* — Nathan R Price
*Assistant Examiner* — Tasnim Mehjabin Ahmed
(74) *Attorney, Agent, or Firm* — Monty L Ross PLLC; Monty L. Ross (57) ABSTRACT

A syringe for medical use, the syringe having a selectively retractable needle and a multifunctional needle holder and retainer ring assembly including a needle holder with a head section having an inwardly tapering frustoconical section of the fluid pathway and a rearwardly facing annular surface surrounding the rear opening, and an elastomeric retainer ring with a substantially unexpanded collar extending rearwardly beyond the rearwardly facing annular surface to increase needle pushout force, reduce activation force and improve fluid flow through the syringe. Annular projections inside the retainer ring and on the outer surface of the head section of the needle holder are also disclosed.

1 Claim, 6 Drawing Sheets

(56) References Cited

U.S. PATENT DOCUMENTS

2006/0253074 A1\* 11/2006 Thayer ................ A61M 5/3234
                                                            604/110
2007/0255212 A1    11/2007 Smith et al.
2012/0004621 A1     1/2012 Shaw et al.
2015/0174339 A1     6/2015 Bokelman et al.

\* cited by examiner

SYRINGE WITH MULTIFUNCTIONAL NEEDLE HOLDER AND RETAINER RING ASSEMBLY

FIELD OF THE INVENTION

This invention relates to a medical syringe having a barrel, a forwardly projecting needle, a needle retraction assembly seated inside a front part of the barrel, a plunger assembly slidably engaging the inside wall of the barrel from the rear and coaxially aligned with the needle retraction assembly, and a needle retraction cavity disposed inside the plunger assembly that becomes accessible during needle retraction. More particularly, this invention relates to a medical syringe in which the needle retraction assembly desirably further comprises a newly configured multifunctional needle holder and retainer ring assembly having redesigned, cooperatively configured structural elements producing functional capabilities and performance characteristics superior to those of syringes disclosed in the prior art.

RELATED ART

Syringes having selectively retractable needles and coaxially aligned needle retraction cavities are well known, having previously been disclosed, for example, in U.S. Pat. Nos. 5,084,018; 5,114,410; 5,211,629; 5,578,011; 5,632,733; 6,090,077; 6,572,584; 7,351,224; 7,947,020; and 9,642,970. Retractable Technologies, Inc. produces and markets one brand of such syringes under the VanishPoint® trademark. VanishPoint® syringes are available in various sizes and embody a needle retraction mechanism in which a needle holder is biased rearwardly by a compressed coil spring and is held in place prior to retraction by an elastomeric retainer ring disposed between the head of a needle holder and the inside wall of the barrel.

Prior to use of such a syringe, several different factors and force components can affect and act upon various portions and structural elements of the syringe. These factors and forces are desirably considered and properly balanced in order for the syringe components to remain stable in their desired pre-use positions and to perform effectively at the time of use. One of the principal force components exerted on the needle holder by the retainer ring arises from the elasticity of the retainer ring, which helps oppose the rearwardly directed biasing force that is exerted against the needle holder by the compressed coil spring.

The elastomeric retainer ring of the prior art devices has a toroidal configuration with a cylindrical, longitudinally extending inner wall that is substantially the same length as the head portion of the needle holder. The inside diameter of the retainer ring is smaller than the outside diameter of the head portion. During assembly of the prior art needle holder and retainer ring assembly, the head of the needle holder is inserted axially into the elastomeric retainer ring. During insertion, the inner wall of the elastomeric retainer ring is expanded radially outward along its full length to receive the advancing head of the needle holder. When the rearwardly facing surface of the needle holder head is laterally aligned with the rear end of the elastomeric retainer ring, the full length of the inner wall of the elastomeric retainer ring squeezes radially inward against the outer wall of the needle holder. This inwardly directed squeezing force is part of the holding force that impedes rearward sliding movement of the needle holder during assembly, storage and use of the syringe prior to needle retraction.

Because the rearwardly facing ends of the elastomeric retainer ring and the head of the needle holder as previously disclosed are substantially aligned as mentioned above, they cooperate to form a substantially continuous, transverse, rearwardly facing annular surface area around the opening at the rear of the needle holder. This annular surface area is typically greater than the area of the rear opening and is substantially transverse to the inside wall surface of the axial bore of the needle holder, which defines part of the fluid flow path. FIG. 1 of U.S. Pat. No. 6,090,077 depicts, for example, a prior art syringe having a retractable needle wherein the relatively flat, transverse, rearwardly facing annular surface area surrounding the rear opening into the head of the needle holder is substantially greater than the area of the rear opening. In some cases, the inside wall surface of the rear opening tapers radially inward to a slight degree in the forward direction, but not sufficiently to smooth the entry of a medicinal fluid into the fluid flow path of the needle holder when the fluid is pushed forwardly by an advancing plunger during an injection.

The transversely extending annular surface area created by the rearwardly facing annular surfaces of the cooperating needle holder and elastomeric retainer ring are believed to function as a "wall" that hinders laminar flow of a medicinal fluid into and through the needle holder. This increases turbulence and the formation of eddy currents around the opening into the needle holder and also increases the thumb force that must be exerted on the plunger handle by a clinician to expel liquid out of the barrel and into and through the needle holder and needle. This increase in required thumb force, which is more pronounced when administering viscous liquids containing large molecules, such as penicillin, is also believed to affect the balance of the force components necessary to resist relative sliding movement between the elastomeric retainer ring and the needle holder during use of the syringe prior to needle retraction.

As a result, users of these prior art syringes have also experienced instances where one or more air bubbles have become "trapped" in the wide annular space behind the needle holder head and the retainer ring by a medicinal liquid drawn into the syringe barrel during preparation of an injection. Such air bubbles can be difficult to expel through the needle holder prior to an injection, which undesirably increases medication preparation time and can lead to an erroneous perception by a healthcare worker or other user that the dose accuracy has been altered.

Other users of these conventional syringes have observed occasional instances where the head of the needle holder is pushed rearwardly out of engagement with the retainer ring while inserting the needle tip through a stopper in a medicine vial when preparing an injection, thereby accidentally triggering needle retraction prematurely and rendering the syringe inoperative and unusable for administering an injection. Such an occurrence is sometimes referred to as "needle push-through" or "needle push-out," and the associated force required to overcome the holding force exerted on the needle holder by the retainer ring is referred to as the "push-out force."

A syringe with a selectively retractable needle is needed that can improve fluid flow from the barrel into the needle holder, that can reduce or eliminate air bubble formation or accumulation behind the needle holder and retainer ring, and can also reduce the likelihood of needle push-out during normal use. At the same time, a syringe is needed that can exhibit these advantages without increasing the activation force required to initiate needle retraction following an injection, without the necessity of retooling the syringe barrel and without reducing the shelf-life over which such syringes can be expected to remain effective and exhibit these advantages.

SUMMARY OF THE INVENTION

The medical syringe of the invention desirably comprises a barrel, a plunger assembly slidably engaging an inside wall of the barrel, a forwardly projecting needle that is selectively retractable into a coaxially aligned needle retraction cavity disposed inside the plunger assembly. The needle is considered to be "selectively retractable" because the needle and the needle holder to which the needle is securely attached are biased rearwardly prior to needle retraction and are released when needle retraction is initiated as the plunger assembly is fully depressed inside the barrel following an injection. Prior to needle retraction, a multi-functional needle holder and retainer ring assembly holds the needle in a stable, seated position inside a forward portion of the barrel and opposes a rearwardly directed biasing force exerted on the needle holder by a compressed coil spring. At the same time, a plug or other barrier that is part of the plunger assembly blocks access into needle retraction cavity to prevent liquid from entering the needle retraction cavity during an injection. Following an injection, needle retraction occurs when the plunger assembly is advanced inside the barrel, displacing the barrier to the needle retraction cavity and pushing the retainer ring is forward and out of engagement with the needle holder. The compressed spring then expands rapidly toward the rear of the syringe and propels the needle holder and at least part of the needle rearwardly into the needle retraction cavity. When in this post-retraction position, the front tip of the needle no longer projects forwardly from the syringe barrel, thereby protecting patients and others against the undesirable potential consequences of accidental needle sticks.

With the present invention, the needle holder and retainer ring assembly is structurally redesigned and cooperatively reconfigured to produce significant benefits and advantages in assembly, storage and use of the subject devices as compared to the prior art devices. Such benefits and advantages include, for example, facilitating assembly of the syringe, improving the fluid flow profile through the syringe, increasing the needle push-out force to reduce the likelihood of premature needle retraction, reducing the thumb force needed to expel fluid from the syringe barrel into and through the needle holder and needle, and reducing the activation force required to initiate needle retraction without reducing the shelf life over which such benefits are achievable, and without retooling the syringe barrel.

In one embodiment of the invention, a syringe having a retractable needle and a cooperatively configured needle holder and retainer ring assembly is disclosed in which the unexpanded diameter of the inwardly facing wall of the retainer ring is less than the outside diameter of the head section of the needle holder, and in which the axial length of the head section of the needle holder is less than the axial length of the elastomeric retainer ring. When configured in this way, a portion of the inwardly facing wall of the retainer ring extends rearwardly behind the head of the needle holder, remains unexpanded following assembly and forms a circumferentially extending, smaller-diameter elastomeric collar that impedes rearward movement of the needle holder relative to the retainer ring, thereby contributing to an increase in needle push-out force exhibited by the syringe. Additionally, where the length of the head section of the needle holder is reduced relative to the coaxial length of the elastomeric retainer ring and the dimensions of the retainer ring prior to assembly remain the same, the smaller diameter of the unexpanded portion of the elastomeric retainer ring extending rearwardly behind the needle holder is believed to cooperate with the associated reduction in surface area of the outside wall of the head section of the needle holder that is contacted by the inwardly facing surface of the retainer ring to reduce the activation force required to initiate needle retraction following an injection.

In one embodiment of the invention, a syringe having a retractable needle and a cooperatively configured needle holder and retainer ring assembly is disclosed in which the fluid flow profile forwardly into and through the needle holder from the syringe barrel is improved by providing a needle holder and retainer ring assembly in which a circumferentially extending portion of the elastomeric retainer ring extends rearwardly of the head section of the needle holder and cooperates with a wider and more angular coaxially aligned, frustoconical, inwardly facing wall surface located inside a rear opening in the head of the needle holder. This configuration reduces the contiguous lateral surface area disposed around the rear opening, provides more laminar fluid flow through the needle holder and thereby reduces both the thumb force required to administer injections (particularly advantageous with more viscous medicines) and the likelihood that one or more air bubbles will hang up behind rearwardly facing annular surfaces of the needle holder and retainer ring.

In one embodiment of the present invention, a syringe having a selectively retractable needle and a multifunctional needle holder and retainer ring assembly is disclosed in which the needle holder further comprises a front portion having an elongate section extending forwardly through a compressed coil spring and a rear portion comprising a larger diameter head section with a forwardly facing annular surface that abuts against a rear end of the coil spring. A continuous fluid pathway that is coaxially aligned with the needle extends from the needle tip to the rear of the needle holder, which is in direct fluid communication with the fluid chamber inside the syringe barrel. The head section of the needle holder further comprises a rear end having a relatively narrow, rearwardly facing annular surface bounded at its outer edge by a substantially cylindrical sidewall of the head section and bounded at its inner edge by an opening into a frustoconical wall section of the fluid pathway having a surface that tapers inwardly in the forward direction. Providing a wider, frustoconical opening into the fluid pathway at the rear (or proximal) end of the needle holder reduces the width of the transverse annular surface area contiguous to the opening at the rear end of the needle holder, provides a more laminar flow profile into the fluid flow path through the needle holder, and thereby reduces the space available for air bubble formation, accumulation or "hang-up" around the rear opening into the needle holder when preparing a syringe containing an injectable liquid for use in administering an injection. While administering an injection using a syringe with the cooperatively configured needle holder and retainer ring of the invention, less thumb force is required to expel a liquid medicine from the barrel into the fluid flow path through the needle holder.

In one embodiment of the invention, the frustoconical wall surface is inclined at an acute angle ranging from about 40° to about 50°, and most preferably about 45°, from the longitudinal axis through the needle holder. It should be understood, however, that the preferred angle of inclination from the longitudinal axis can depend upon other factors including, for example, the length and diameters of the needle holder and the rear opening into the fluid pathway, the rearward extension of the retainer ring as discussed below and upon the inside configuration of the syringe barrel. The retainer ring will desirably not extend rearwardly behind the needle holder to an extent that it will impede delivery of a complete dose of liquid during an injection or increase the activation force needed to initiate needle retraction. Also, the acute angle of inclination of the frustoconical inside wall surface of the head section of the needle holder relative to the longitudinal axis through the needle holder is desirably not so great that it causes the radial width of the rearwardly facing annular surface around the rear opening into the needle holder to become so narrow that the rear end portion of the head section of the needle holder can be deformed or partially collapse when subjected to the inwardly directed compressive forces exerted on the outside wall of the head section by the retainer ring and the barrel during or after assembly but prior to use of the syringe.

The reduction in the space available for air bubble hang-up is further enhanced by cooperatively configuring the unexpanded, rearwardly facing portion of the retainer ring to extend rearwardly beyond the rear end of the head section of the needle holder. This configuration forms a rearwardly extending circumferential collar around the rear end of the head section of the needle holder that significantly reduces the substantially coplanar, lateral surface area around the rear opening into the needle holder as compared, for example, to prior art syringes where the rearwardly facing surfaces of both the needle holder and the retainer ring are collectively wider, substantially coplanar and transverse to the longitudinal axis through the needle holder. In one embodiment of the invention, the retainer ring extends behind the rear end of the needle holder by a distance that is less than the radius of the head section and is preferably approximately equal to the width of the rearwardly facing annular surface of the head section around the rear opening into the head section. In one embodiment of the invention, when the needle holder and the retainer ring are cooperatively configured in this way, a line lying in the frustoconical wall section and intersecting the longitudinal axis of the fluid pathway will also desirably intersect the rearwardly extending portion of the retainer ring tangentially at a point proximal to the proximal end of the retainer ring. As a result, the area and volume available for bubble formation, accumulation or hang-up behind the needle holder and retainer ring assembly is reduced and axially staggered, and any bubble formed is more likely to be carried forward into the fluid pathway by a more laminar flow of liquid being injected through the syringe.

In one embodiment of the invention, the rearwardly facing annular surface around the rear opening of the needle holder has a width that is approximately equal to the distance by which the axially and circumferentially extending, radially unexpanded collar portion of the retainer ring extends rearwardly beyond the rearwardly facing annular surface of the head section of the needle holder.

In another embodiment of the invention, the rear opening of the needle holder has a radius and the rearwardly extending portion of the retainer ring extends behind the rear end of the needle holder by a longitudinal distance that is less than the radius of the rear opening.

In another embodiment of the invention, the head section of the needle holder has a first radius, the rear opening in the head section has a second radius, and the rearwardly extending portion of the retainer ring extends past the rear end of the needle holder by a longitudinal distance that is between the first and second radius.

In one embodiment of the invention, a syringe having a selectively retractable needle and a multifunctional needle holder and retainer ring assembly is disclosed in which at least one of the inwardly facing surface of the retainer ring and the outwardly facing surface of a head section of the needle holder comprises an annular projection that is desirably configured to enhance frictional interference between the head section of the needle holder and the retainer ring while still permitting relative sliding movement between them during needle retraction. Such frictional interference can help maintain the position of the needle holder relative to the retainer ring prior to use of the syringe and during an injection, and can help resist fluid leakage between the needle holder and the retainer ring during an injection. The configuration of the annular projection also desirably allows forward sliding movement of the retainer ring along the outside wall of the head of the needle holder when the retainer ring is subjected to plunger pressure applied by the user during needle retraction following an injection. It should also be appreciated that needle retraction is desirably initiated by the continued application of substantially constant pressure at the end of an injection, which should in most cases cause the needle tip to be withdrawn from the patient and retracted into the syringe body automatically in one smooth, continuous motion.

In one embodiment of the invention, a syringe having a selectively retractable needle and a multifunctional needle holder and retainer ring assembly is disclosed in which the retainer ring embodies an inside surface further comprising an annular projection facing radially inward that is configured to slidably engage the outwardly facing, substantially cylindrical sidewall of the head section of the needle holder.

In one embodiment of the invention, a syringe having a selectively retractable needle and a multifunctional needle holder and retainer ring assembly is disclosed in which the retainer ring embodies an inside surface with an annular projection facing radially inward, the annular projection having a cross-section generally configured as a truncated prism with oppositely inclined proximal and distal surface surfaces and a substantially flat, inwardly facing surface disposed between them.

In one embodiment of the invention, a syringe having a selectively retractable needle and a multifunctional needle holder and retainer ring assembly is disclosed, the assembly further comprising an outwardly facing annular projection on an otherwise cylindrical sidewall section of a head section of the needle holder, the outwardly facing annular projection further comprising a forwardly inclined rear surface, a front surface transverse to the longitudinal axis through the needle holder, and a substantially flat inwardly facing surface disposed between them to facilitate forward axial slidable movement of the retainer ring relative to the head section of the needle holder and to impede rearward axial slidable movement of the retainer ring relative to the head section of the needle holder.

One advantage observed through use of the disclosed invention relates to improved (less turbulent; more laminar) fluid flow from the barrel into the needle holder and the associated reduction in air bubble formation, accumulation or hang-up behind the needle holder and retainer ring during medication preparation, thus reducing medication preparation time and promoting user confidence in dose accuracy as well as reducing the thumb force required to expel medicinal fluid from the syringe at a desired rate. This in turn allows a medicinal fluid to be injected more quickly, which reduces the injection time and the period during which a needle is insert into a patient's body and also reduces the pain and discomfort experienced by a patient who is receiving an injection.

Another advantage observed through use of the disclosed invention relates to an increase in the "push-out" force required to trigger needle retraction prematurely when inserting a needle into the stopper of a medicine when preparing for an injection. Another advantage observed through use of the disclosed invention is a reduction in the activation (functionality) force required to initiate needle retraction following an injection. An ancillary benefit believed to be achievable through use of the inventions disclosed here is improved (extended) shelf-life without resultant drop-offs in product performance or increases in activation force as demonstrated by accelerated aging tests.

Other potential benefits and advantages are also believed to be achievable through use of the cooperatively configured needle holder and retainer ring assembly of the invention in a syringe having a retractable needle. One such benefit relates to a syringe having a needle holder and retainer ring assembly that is better adapted to withstand adverse environmental conditions, maintain its structural integrity and achieve its performance objectives following prolonged storage or after being subjected to rough handling. Another potential benefit relates to a syringe having a needle holder and retainer ring assembly that reduces the likelihood of premature blowout of the retainer ring during an injection of a fluid having a relatively high viscosity or during a "fast push" injection of a less viscous fluid by clinical personnel. Another potential benefit relates to a syringe having a needle holder and retainer ring assembly that reduces the likelihood of fluid leakage between the retainer ring and the inside surface of the syringe barrel prior to initiating needle retraction.

It should also be appreciated that a syringe comprising the needle holder and retainer ring assembly of the invention as disclosed here is suitable for use with plunger assemblies having plunger handles with front ends with various configurations including, for example, tubular, stepped-front or inclined front ends. The selection of a particular configuration for the front end of the plunger handle can depend at least in part upon whether it is desired to distribute the thumb force delivered through the plunger handle evenly around the circumference of a retainer ring or to concentrate all or a portion of the forwardly directed force generated by the plunger against one side or arcuate portion of the retainer ring. Concentrating the thumb force on one side or section of the retainer ring can help in overcoming inertia to initiate forward sliding movement of the retainer ring relative to the needle holder and barrel, or to overpressure any structural element projecting from the needle holder, retainer ring or barrel that resists relative movement between them prior to initiating needle retraction.

BRIEF DESCRIPTION OF THE DRAWINGS

The apparatus of the invention is further described and explained in relation to the following drawings wherein.

It should be appreciated that the accompanying drawings are not drawn to scale.

DESCRIPTION OF THE PREFERRED EMBODIMENTS

Figure 1:
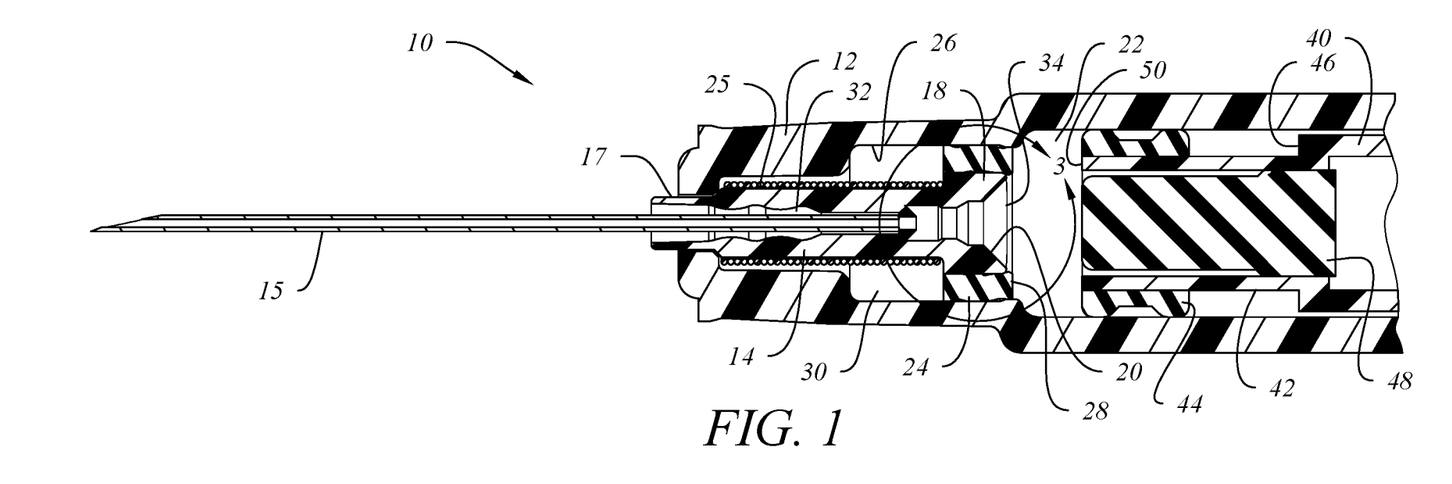
FIG. 1 is a longitudinal cross-sectional view through the front end of a medical syringe configured according to one embodiment of the invention and having an installed needle and needle retraction mechanism, an elastomeric retainer ring, and a slidably engaged plunger assembly (partially broken away) with a plug blocking access into a needle retraction cavity.
Figure 5:
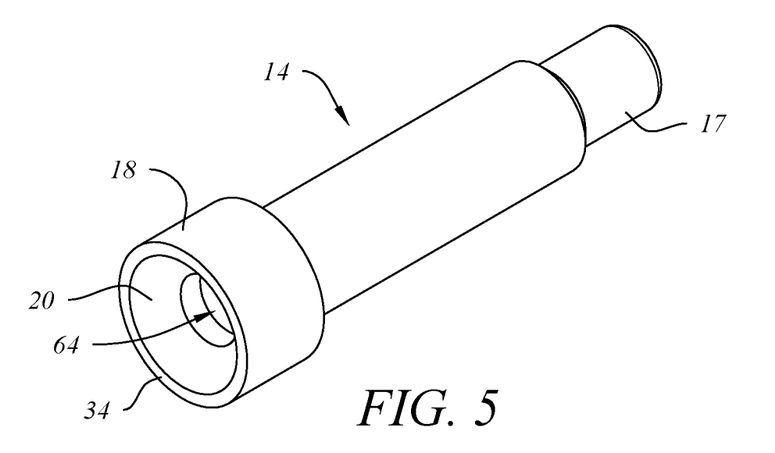
FIG. 5 is a rear perspective view of a needle holder suitable for use in a syringe configured according to the embodiment of FIG. 1.
Figure 6:
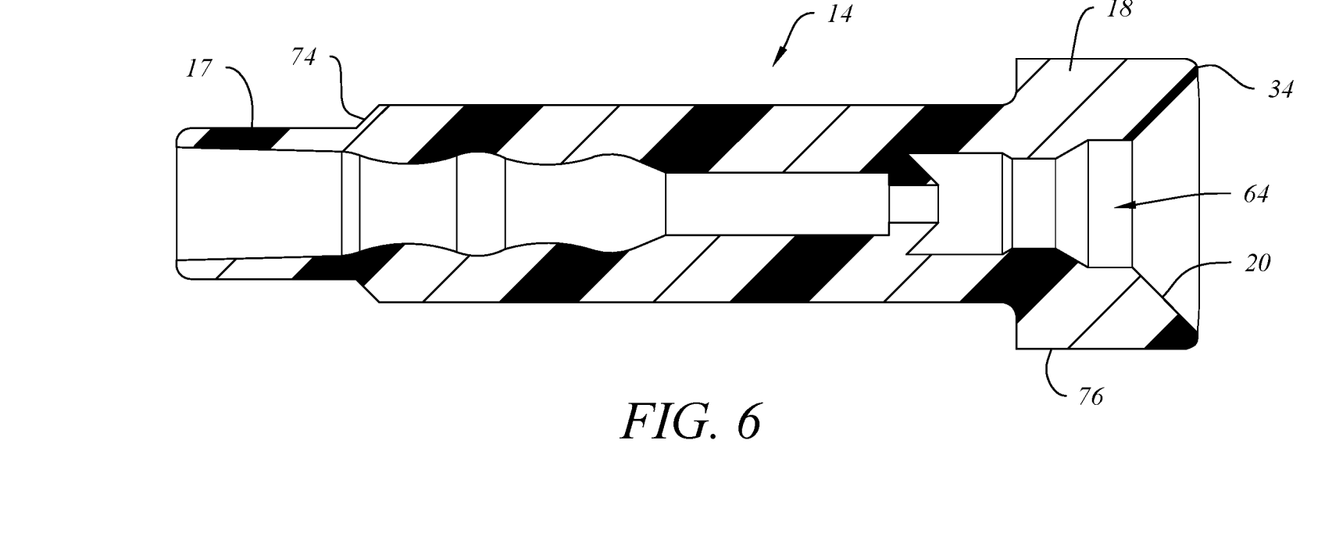
FIG. 6 is an enlarged longitudinal cross-sectional view of the needle holder of FIG. 5.
Figure 7:
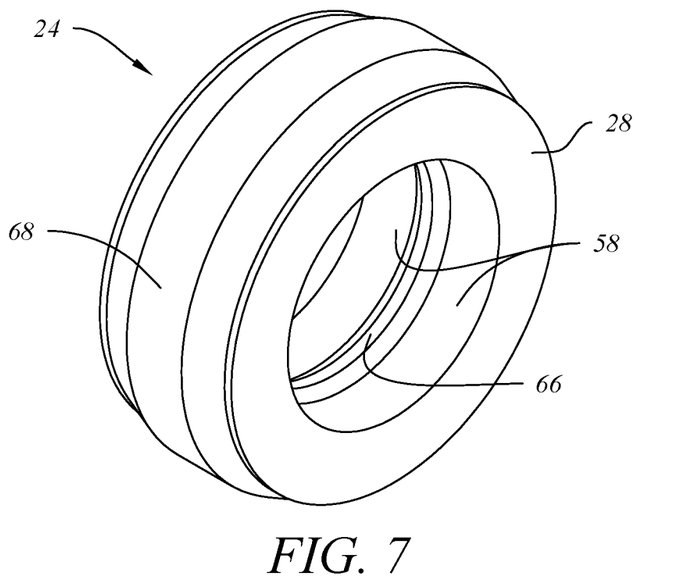
FIG. 7 is a rear perspective view of a retainer ring suitable for use in one embodiment of the syringe of FIG. 1.
Figure 8:
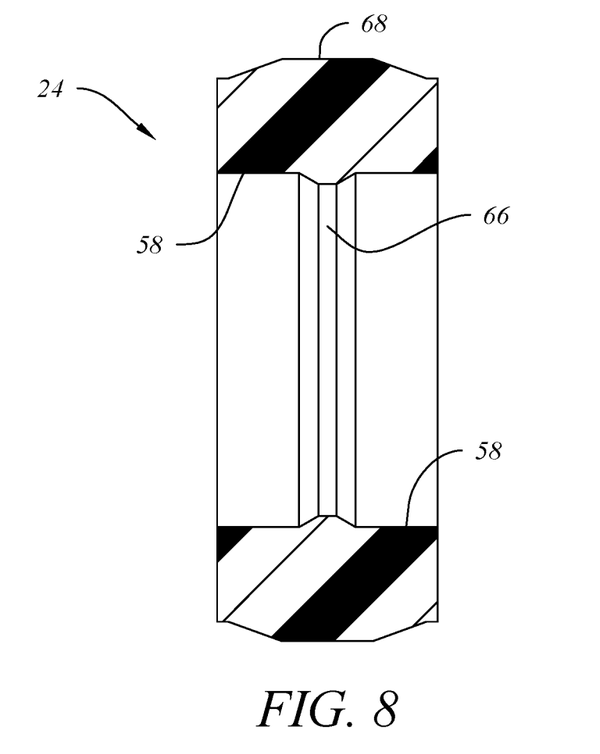
FIG. 8 is a longitudinal cross-sectional view through the retainer ring of FIG. 7.

Referring to syringe 10 as shown in FIG. 1, the rear portion of barrel 12 and plunger 40 of syringe 10 are broken away to permit enlargement of the elements disposed at the front of syringe 10. Referring to FIGS. 1, 5 and 6, inclined shoulder 74 (FIG. 6) of needle holder 14 is seated inside a nose portion of barrel 12, with front tip 17 of needle holder 14 projecting forwardly through an opening in the distal end of the nose portion. Needle 15 has a forwardly projecting beveled tip and a rear portion that is secured by conventional means in fixed relation to a variable diameter axial bore 32 through the needle holder 14. The proximal end of needle holder 14 has a head section 18 with a larger diameter outer wall 76 that forms a forwardly facing annular shoulder. The annular shoulder abuts against the proximal end of compressed coiled spring 25 when spring 25 is seated inside the nose portion of barrel 12 around an elongate section of needle holder 14 that extends between inclined shoulder 74 and the distal end of outer wall 76 of head section 18. In this configuration, when coiled spring 25 is compressed during assembly of syringe 10, it biases needle holder 14 rearwardly relative to the nose portion of barrel 12.

Figure 11:
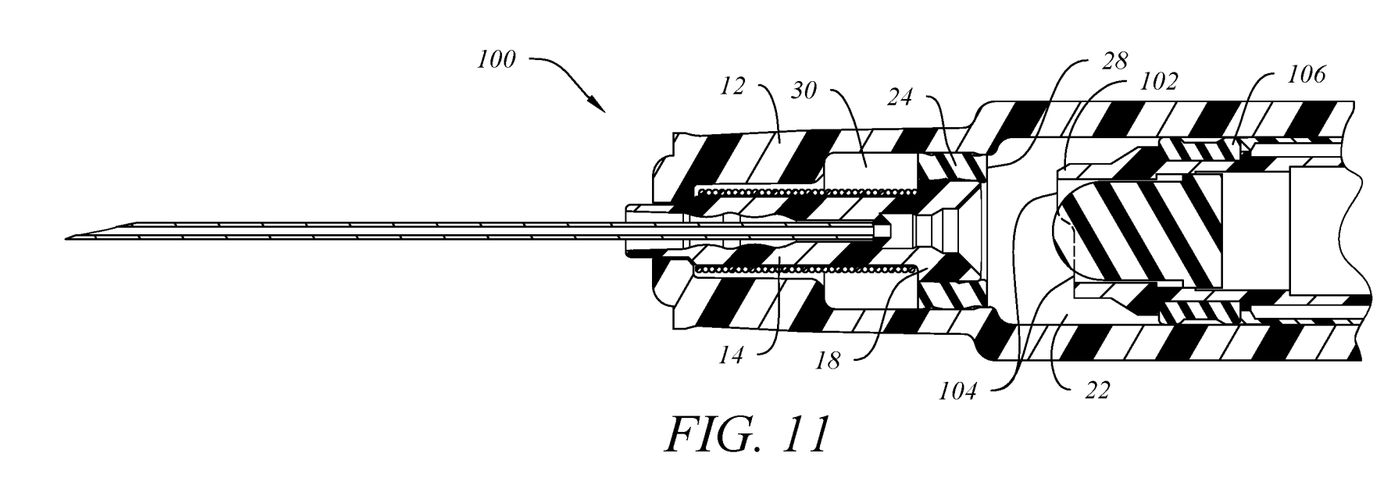
FIG. 11 is a longitudinal cross-sectional view of an alternate embodiment of the syringe as in FIG. 1 wherein the front end of the handle of the plunger assembly is stepped rearwardly to cause one side of the front end of the plunger handle to concentrate a thumb force applied to the plunger on one side of the retainer ring.
Figure 12:
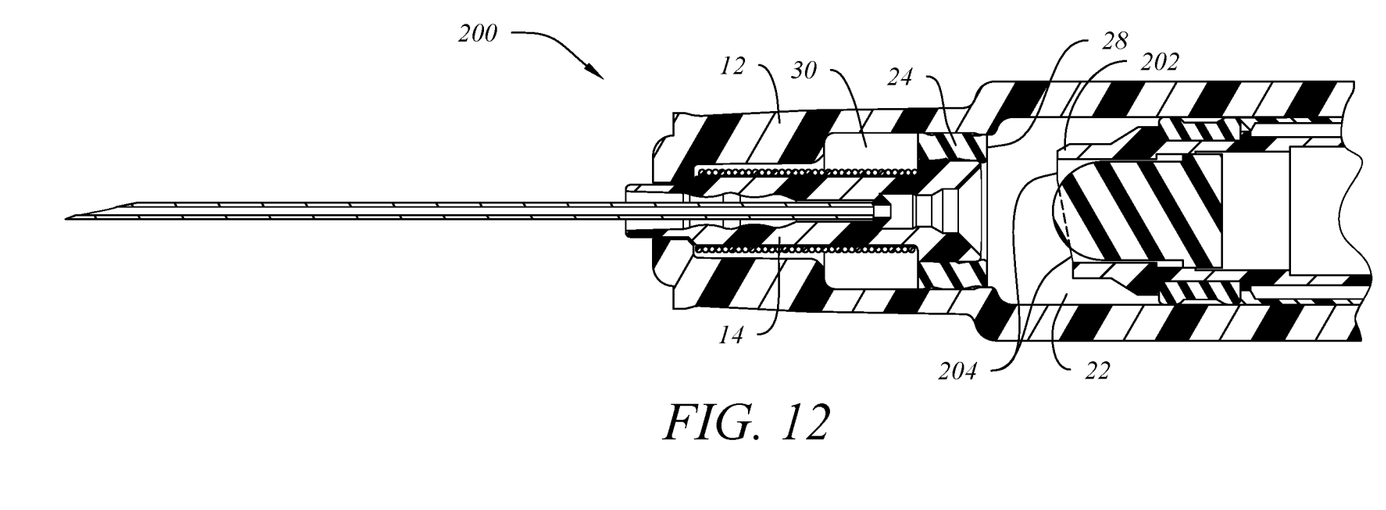
FIG. 12 is a longitudinal cross-sectional view of the apparatus as in FIG. 11 wherein the front end of the handle of the plunger assembly is inclined rearwardly to cause one side of the front end of the plunger handle to concentrate a thumb force applied to the plunger on one side of the retainer ring.

Although plunger 40 as shown in FIG. 1 is made with plunger seal 44 that can slide rearwardly to a point where it abuts forwardly facing annular shoulder 46 of plunger 40 as plunger tip 50 is moved forward relative to barrel 12 by the application of thumb force during an injection. By contrast, syringe 100 seen in FIG. 11 is made with a differently configured plunger tip 104 and a plunger seal 106 that is held in place between two annular shoulders and cannot slide axially relative to the plunger handle during an injection. The multifunctional needle holder and retainer ring of the invention is nevertheless applicable to syringes having either plunger configuration.

Referring again to FIG. 1, elastomeric retainer ring 24 is made with an inside diameter that is less than the outside diameter of head section 18 and the front portion of elastomeric retainer ring 24 is desirably expanded during insertion of head section 18 during assembly so to facilitate insertion of axially extending outer wall 76 of head section 18 of needle holder 14. Following insertion of head section 18 into the front portion of elastomeric retainer ring 24 and after retainer ring 24 is disposed between head section 18 of needle holder 14 and inside wall section 26 of barrel 12, elastomeric retainer ring 24 exerts sufficient holding force against head section 18 of needle holder 14 to resist relative motion or fluid leakage around retainer ring 24 during use of syringe 10 prior to needle retraction. Other performance benefits as discussed herein are also achieved through use of the structurally modified multifunctional needle holder and retainer ring assembly of the invention. As used herein, the term "multifunctional needle holder and retainer ring assembly" (or simply "needle holder and retainer ring assembly" as used below) is understood to include the installed combination of needle holder 14 and retainer ring 24 in a syringe 10 of the invention. This cooperatively configured combination of elements is discussed in greater detail below in relation to FIGS. 1-10 of the drawings.

Another feature of the present invention is disclosed and described in relation to FIGS. 1, 5 and 6. Proximal end 34 of head section 18 comprises an opening into a proximal portion of variable diameter bore 32 of needle holder 14 that further comprises a frustoconical section having a wall surface 20 disposed in the proximal end portion of head section 18 of needle holder 14. The inside diameter of frustoconical wall surface 20 at proximal end 34 is desirably greater than the inside diameter of rear openings of the needle holders of similarly made conventional syringes. It is also sufficiently less than the outside diameter of head section 18 at proximal end 34 of needle holder 14 that proximal end 34 of head section 18 can withstand compressive forces exerted on it by elastomeric retainer ring 24 without deformation or collapse. This feature produces a relatively narrow, rearwardly facing annular surface around the rear opening at proximal end 34 of needle holder 14.

Frustoconical interior wall surface 20 of head section 18 tapers radially inward forwardly of proximal end 34 and forms a proximal end of fluid flow path 64 through needle holder 14 that is more conducive to receiving a smooth flow of liquid from interior chamber 22 of barrel 12 (FIG. 1) into needle holder 14, thereby contributing to a reduction in the thumb force needed for a user of syringe 10 to advance plunger 40 inside barrel 12 during an injection. The diameter of bore 32 defining fluid flow path 64 decreases at a substantially constant rate until a point is reached where the constant convergence of wall surface 20 ends and the inside diameter of axial bore 32 is differently configured to accommodate the insertion and secure attachment of needle 15 inside needle holder 14. This needle holder configuration provides an inwardly tapering fluid flow path 64 for a medicinal fluid pushed by a plunger assembly from barrel 12 into needle 15 during an injection using medical syringe 10.

The combination of a narrower rearwardly facing annular surface extending around and a wider, rear opening at proximal end 34 of needle holder 14 cooperate to reduce the accumulation or hang-up of small air bubbles in the space identified by arrow 29 (visible in FIGS. 9, 10, 11-12) around the opening at proximal end 34 of needle holder 14. In one embodiment of the invention, the frustoconical section inside the rear opening of head section 18 of needle holder 14 has a wall surface 20 inclined at an acute angle ranging from about 40° to about 50°, and preferably about 45°, from the longitudinal axis 102 (visible in FIGS. 9-10) of needle holder 14. In another embodiment of the invention, line 100 (visible in FIGS. 4, 9-10) lying in wall surface 20 of the frustoconical section and intersecting longitudinal axis 102 of the needle holder also intersects the rearwardly extending portion of the retainer ring tangentially at a point closely adjacent to the rear end of the retainer ring.

By narrowing the width of proximal end surface 34 while maintaining a constant outside diameter for head section 18 of needle holder 14 and widening the opening defined by the proximal edge of interior surface section 20 of needle holder 14, a smoother flow profile into fluid flow path 64 (FIG. 3) is established and less transverse surface area is provided at proximal end 34 of needle holder 14 on which air bubbles can otherwise accumulate behind needle holder 14. Such air bubbles sometimes concern patients or clinicians, or cause such persons to perceive that an incomplete dose is being administered through syringe 12. Also, in contrast to conventional retractable syringes, because the annular surfaces of proximal end 34 of needle holder 14 and proximal end 28 of retainer ring 24 are not transversely aligned, the proximal ends of needle holder 18 and retainer ring 24 cannot collectively provide a wider contiguous surface upon which air bubbles can accumulate around the rear opening of the needle holder prior to or during an injection.

Figure 3:
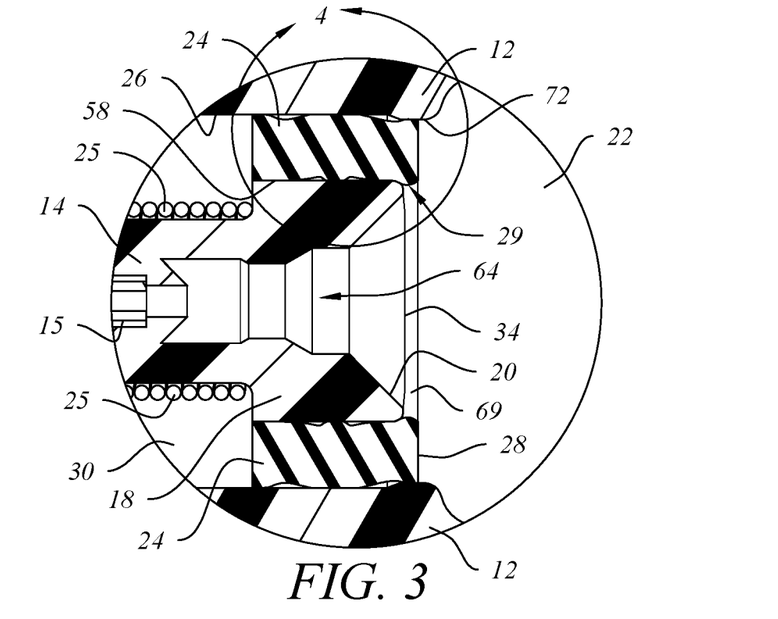
FIG. 3 is an enlarged cross-sectional detail view taken from FIG. 1.
Figure 4:
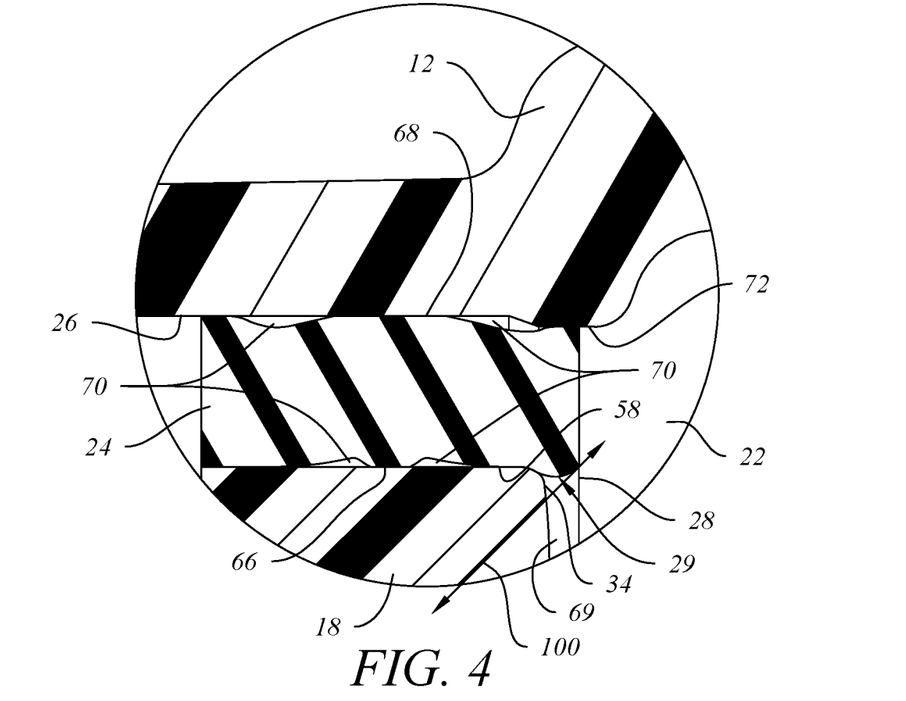
FIG. 4 is an enlarged cross-sectional detail view taken from FIG. 3.

In another preferred embodiment of the invention that is described in relation to FIGS. 1, 3 and 4, syringe 10 having a selectively retractable needle 15 that also comprises a multifunctional needle holder and retainer ring assembly is disclosed in which unexpanded proximal end 28 of retainer ring 24 extends rearwardly past proximal end 34 of needle holder 14 for a short distance that is preferably not significantly greater than the radial width of the annular surface at proximal end 34 of needle holder 14. This rearward extension of retainer ring 24 relative to needle holder 14 forms a relatively short, axially extending, radially unexpanded annular collar 69 that presses radially inward around proximal end 34 of retainer ring 24. Also, during assembly of syringe 10, inwardly projecting annular "bump" 72 inside barrel 12 can force annular collar 69 formed by the radially unexpanded, rearwardly extending proximal end 28 of retainer ring 24 radially inward behind the outer edge of the annular surface at proximal end 34 of needle holder 14. These factors cooperate to cause proximal end 28 of retainer ring 24 to squeeze inwardly behind outer wall 76 (FIG. 6) at proximal end 34 and thereby reduces the likelihood of rearward slippage of needle holder 14 relative to retainer ring 24 without increasing the activation force required to push retainer ring 24 forwardly off outer wall 76 during needle retraction following an injection.

Where the new multifunctional needle holder and retainer ring assembly of the invention is desired to be retrofitted into a existing syringe barrel configuration of an otherwise similarly configured prior art syringe without barrel redesign or retooling, the axial length of retainer ring 24 is retained and the axial length of head section 18 of needle holder 14 is reduced relative to retainer ring 24 to establish substantially unexpanded annular collar 69 (FIGS. 3-4). Proximal end 34 of head section 18 is then disposed in a position slightly forward of proximal end 28 of retainer ring 24 when retainer ring 24 is satisfactorily installed between the outside wall of head section 18 and inside wall section 26 of barrel 12. At the same time, the distal, forwardly facing surface of retainer ring 24 is desirably substantially even with the distal, forwardly facing annular surface of head section 18 of needle holder 14. Said differently, when retainer ring 24 is slightly compressed between head section 18 and inside wall section 26 of barrel 12 during installation, retainer ring 24 desirably has an axial length that exceeds the axial length of head section 18 of needle holder 14 so that proximal end 28 of retainer ring 24 forms a short, rearwardly extending collar 69 around proximal end 34 of needle holder 14.

In one embodiment of the invention, proximal end 28 of retainer ring 24 extends behind proximal end 34 of needle holder 14 by a distance not significantly wider than the width of the rearwardly facing annular surface at proximal end 34 of needle holder 14. In another embodiment of the invention, a line 100 lying in frustoconical wall section 20 of needle holder 14 and intersecting the longitudinal axis of needle holder 14 and fluid pathway 64 will also preferably tangentially intersect the rearwardly extending, unexpanded portion of the retainer ring 24 at a point closely adjacent to proximal end 28 of retainer ring 24. In each of these preferred embodiments, retainer ring 24 is desirably cooperatively configured together with needle holder 14 so that the rear opening into liquid flow path 64 (FIG. 3) has an inwardly tapered frustoconical wall surface 20 as discussed above.

In another embodiment of the invention that is disclosed and described in relation to FIGS. 1, 3-4 and 7-8, syringe 10 has a selectively retractable needle 15 and also comprises an assembly of multifunctional needle holder 14 and retainer ring 24. Retainer ring 24 desirably further comprises inwardly facing surface sections 58 separated by an inwardly facing annular projection 66 that in this embodiment is configured as a trapezoidal prism having oppositely inclined proximal and distal surfaces extending between one of inwardly facing surface sections 58 and the corresponding side of a substantially flat inner surface 66 disposed between them. In FIGS. 3 and 4, which are progressively enlarged to better depict the facing and contacting surfaces between retainer ring 24 and outer wall 76 (FIG. 6) of head section 18 of needle holder 14, it is observed by comparison with the cross-sectional view of retainer ring 24 in FIG. 8 that body 68 of retainer ring 24 is compressed radially from both the barrel side and the needle holder side during installation of retainer ring 24 between inside wall section 26 of barrel 12 and the outer wall of head section 18 of needle holder 14. This compression enhances the holding force that limits relative axial movement of needle holder 14 relative to retainer ring 24 and of retainer ring 24 relative to inside wall section 26 of barrel 12, and also reduces the likelihood of fluid leakage past retainer ring 24. Distorted air pockets 70 that are best seen in FIG. 4 are also believed to enhance the holding force exerted by retainer ring 24 relative to head section 18 and inside wall section 26 of barrel 12.

Figure 9:
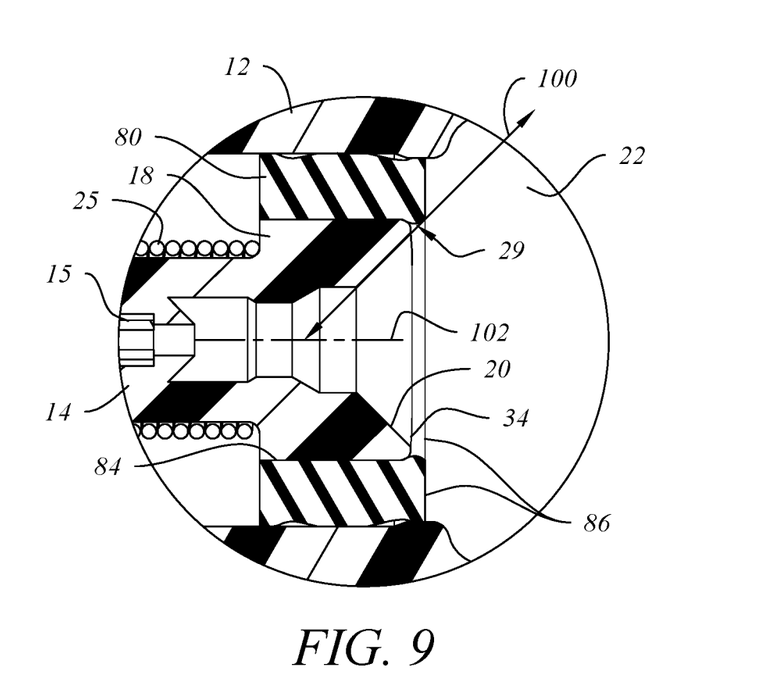
FIG. 9 is an enlarged detail view as in FIG. 3 of an alternate embodiment of the invention wherein the retainer ring is configured differently from the embodiment shown in FIG. 3.

Referring to FIG. 9, another embodiment of the invention is disclosed in which a differently configured retainer ring 80 is installed in combination with needle holder 14 to produce a differently configured multifunctional needle holder and retainer ring assembly. In this embodiment, retainer ring 80 is again lengthened axially or, alternatively, head section 18 of needle holder 14 is shortened relative to retainer ring 80 to again produce a short annular collar having a proximal end 86 that extends rearwardly of proximal end 34 of head section 18. As discussed above in relation to retainer ring 24, the portion of retainer ring 80 extending rearwardly behind head section 18 of needle holder 14 can also compress inwardly behind proximal end 34 of head section 18 of needle holder 14 to increase the axial holding force between them. In this embodiment, however, inwardly facing surface 84 of retainer ring 80 lacks the inwardly facing annular projection as previously shown and described in relation to FIGS. 7-8.

Figure 10:
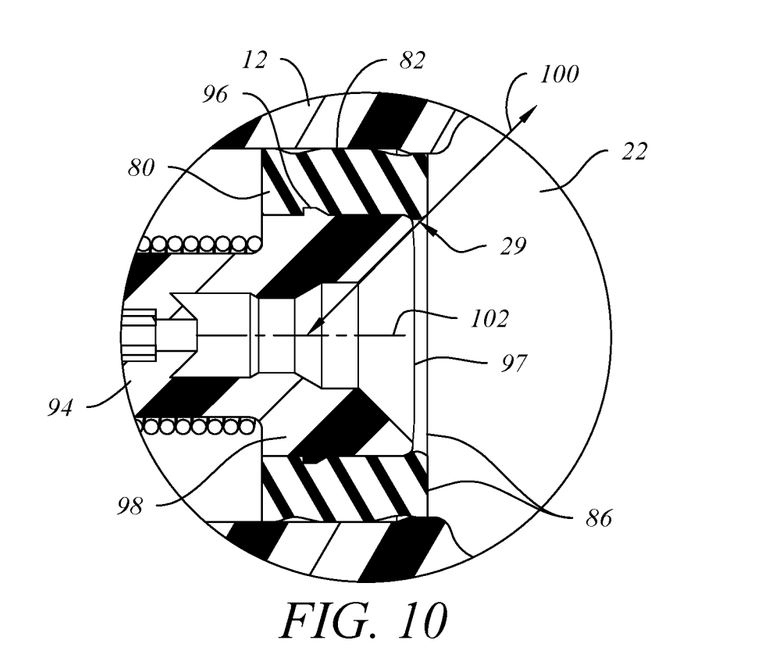
FIG. 10 is an enlarged detail view as in FIG. 3 of another alternate embodiment of the invention wherein the retainer ring and the outer surface of the head of the needle holder are cooperatively configured differently from the embodiment shown in FIG. 3.

Referring to FIG. 10, another embodiment of the invention is disclosed in which retainer ring 80 is installed in combination with needle holder 94 having head section 98 to produce another differently configured multifunctional needle holder and retainer ring assembly. In this embodiment, retainer ring 80 is again lengthened axially or, alternatively, head section 98 of needle holder 94 is shortened relative to retainer ring 80 to again produce a short annular collar having a proximal end 86 that extends rearwardly of proximal end 97 of head section 98. As discussed above in relation to retainer ring 24, retainer ring 80 can also compress inwardly behind proximal end 97 of head section 98 of needle holder 94 to increase the axial holding force between them. In this embodiment, however, the outer wall surface of head section 98 comprises an outwardly facing annular projection 96 having an inclined surface on the proximal side that allows the substantially cylindrical inside surface of retainer ring 80 to slide up and over annular projection 96 during assembly and also during needle retraction following use of syringe 10 as discussed below in relation to FIGS. 1-2 and 11-12. Prior to and during use of syringe 10, however, a forwardly facing square shoulder on the distal side of annular projection 96 will restrict any rearward movement of retainer ring 80 relative to head section 98 of needle holder 94 as might otherwise be experienced, for example, during an instance of needle "push-through.".

Referring again to FIG. 1, during an injection using syringe 10, front end 50 of plunger tip 42 is advanced inside barrel 12, forcing medicinal fluid disposed inside variable volume chamber 22 (not shown) forwardly into the opening disposed at proximal end 34 of needle holder 14, and then through needle holder 14 and needle 15. When front end 50 contacts proximal end 28 of retainer ring 24, the continued application of thumb force to plunger assembly 40 initiates three concurrent movements: Plunger seal 44 begins moving rearwardly toward forwardly facing shoulder 46; retainer ring 24 begins moving forwardly along the interfaces with head section 18 of needle holder 14, eventually pushing retainer ring 24 off of head section 18 and into annular space 30; and plunger plug 48 begins moving rearwardly toward a coaxially aligned needle retraction cavity disposed inside the plunger handle behind plunger plug 48.

Figure 2:
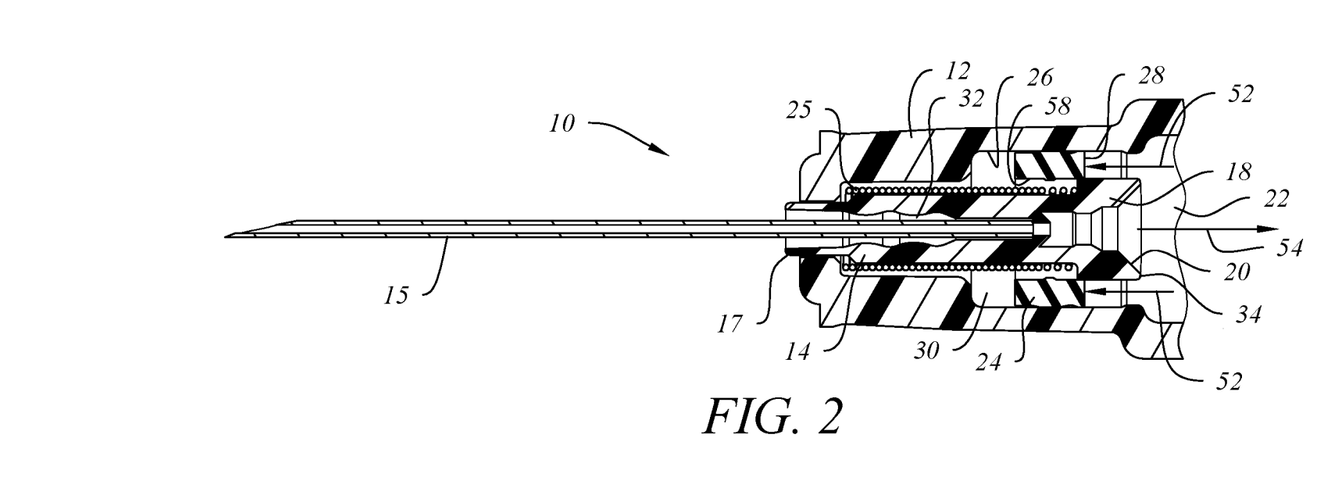
FIG. 2 is a longitudinal cross-sectional view of the apparatus of FIG. 1 with the plunger assembly broken away and the retainer ring moved forwardly relative to the head of the needle holder and the barrel as needle retraction is initiated by forward movement of the plunger assembly (indicated diagrammatically by arrow 52.

Referring to FIG. 2, parts of the plunger assembly are removed for illustrative purposes, arrows 52 depict the direction of movement of retainer ring 24 and arrow 54 depicts the direction of movement of needle holder 14. Retainer ring 24 is shown in a position where it has almost entirely disengaged from needle holder 14, and compressed spring 25 is beginning to expand rearwardly, driving needle holder 14 and needle 15 rearwardly toward the coaxially aligned needle retraction cavity.

Referring again to syringe 10 in FIG. 1, it is seen that front end 50 of plunger tip 42 of plunger assembly 40 is circular and is transverse to the longitudinal axis of syringe 10.

Referring to syringe 100 in FIG. 11, it is seen that front end 104 is stepped back axially on one side of plunger 102, so that one arcuate segment of front end 104 will contact retainer ring 24 before the remainder does, thereby initially concentrating the "thumb force" on one side of retainer ring 24 to assist in sliding it forwardly relative to needle holder 14. Referring to syringe 200 in FIG. 12, it is seen that front end 204 is inclined rearwardly on one side of plunger 202, so that one arcuate segment of front end 204 will contact retainer ring 24 before the remainder does, again initially concentrating the "thumb force" on a relatively short arcuate segment on one side of retainer ring 24, after which the thumb forces is progressively distributed around the remainder of proximal end 28 of retainer ring 24 to assist in sliding retainer ring 24 forwardly relative to needle holder 14.

Other benefits, advantages, embodiments and modifications of the present invention will likely become apparent to those of ordinary skill in the art upon reading this disclosure, and it is intended that the scope of the invention be limited only by the broadest interpretation of the specification and claims to which the inventors and applicants are legally entitled.

What is claimed is:

1. A syringe having a barrel, a plunger assembly, a retractable needle and a cooperatively configured needle holder and retainer ring assembly comprising:
   a head section of the needle holder further comprising a rear opening into a coaxially aligned fluid flow path communicating with the retractable needle and a frustoconical, inwardly facing wall surface located proximally to the rear opening; and
   an elastomeric retainer ring having a first longitudinally extending portion that is expanded radially and surrounds the head section of the needle holder and a second longitudinally extending collar portion that is substantially unexpanded radially and extends rearwardly behind the head section of the needle holder; wherein
   the rearwardly extending collar portion of the elastomeric retainer ring cooperates with the frustoconical, inwardly facing wall surface to reduce a thumb force required to advance the plunger assembly inside the barrel and to reduce turbulence in a fluid entering the rear opening into the fluid flow path during an injection, and to reduce retention of any air bubble in fluid disposed around the opening during use of the syringe.

* * * * *